(12) United States Patent
Hamaguchi et al.

(10) Patent No.: US 8,079,708 B2
(45) Date of Patent: Dec. 20, 2011

(54) EYE REFRACTIVE POWER MEASUREMENT APPARATUS

(75) Inventors: Koji Hamaguchi, Aichi (JP); Mitsuhiro Gono, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 12/890,239

(22) Filed: Sep. 24, 2010

(65) Prior Publication Data

US 2011/0075097 A1      Mar. 31, 2011

(30) Foreign Application Priority Data

Sep. 30, 2009    (JP) ................................. 2009-227808

(51) Int. Cl.
*A61B 3/10*      (2006.01)
(52) U.S. Cl. ......................... 351/205; 351/211; 351/221
(58) Field of Classification Search .................. 351/200, 351/205, 206, 210, 211, 221
See application file for complete search history.

(56) References Cited

U.S. PATENT DOCUMENTS

| 7,416,301 B2 | 8/2008 | Hanebuchi et al. |
| 7,771,050 B2 * | 8/2010 | Honda et al. ................... 351/208 |

* cited by examiner

*Primary Examiner* — Jack Dinh
(74) *Attorney, Agent, or Firm* — Lowe Hauptman Ham & Berner LLP

(57) ABSTRACT

An eye refractive power measurement apparatus measures both eye refractive powers in cases where a pupil is small and large in diameter with ease. This apparatus includes: a measuring optical system causing an imaging device to capture a ring-shaped image based on measurement light reflected from a fundus of an examinee's eye; a light deflecting member arranged at a position, which is not conjugated with a pupil of the examinee's eye, on an optical path of the measuring optical system; a rotor causing the light deflecting member to rotate about an optical axis of the measuring optical system; and an eccentricity amount changer changing an amount of eccentricity of the measurement light, which is rotated eccentrically on a surface of the pupil, with respect to a center of the pupil, in order to change a region, where the measurement light passes, on the surface of the pupil.

6 Claims, 4 Drawing Sheets

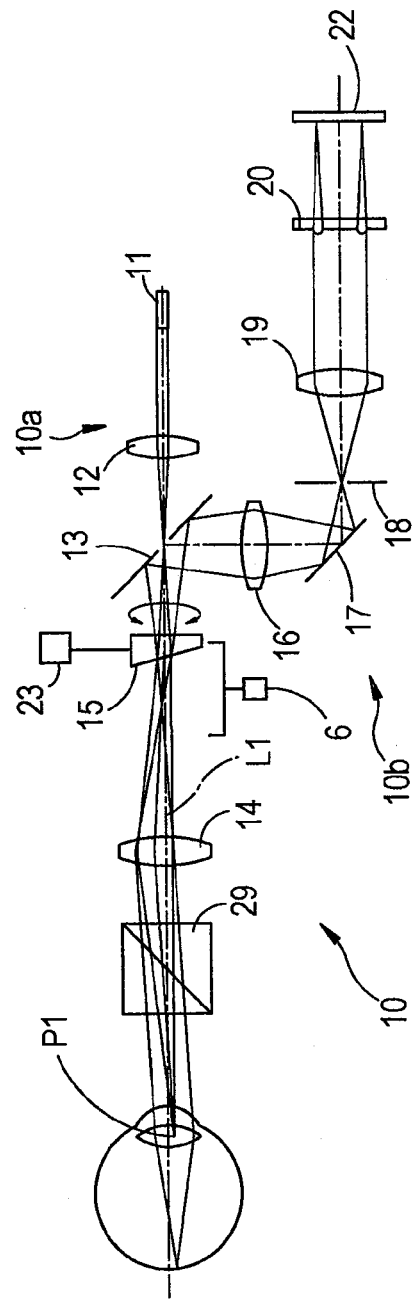
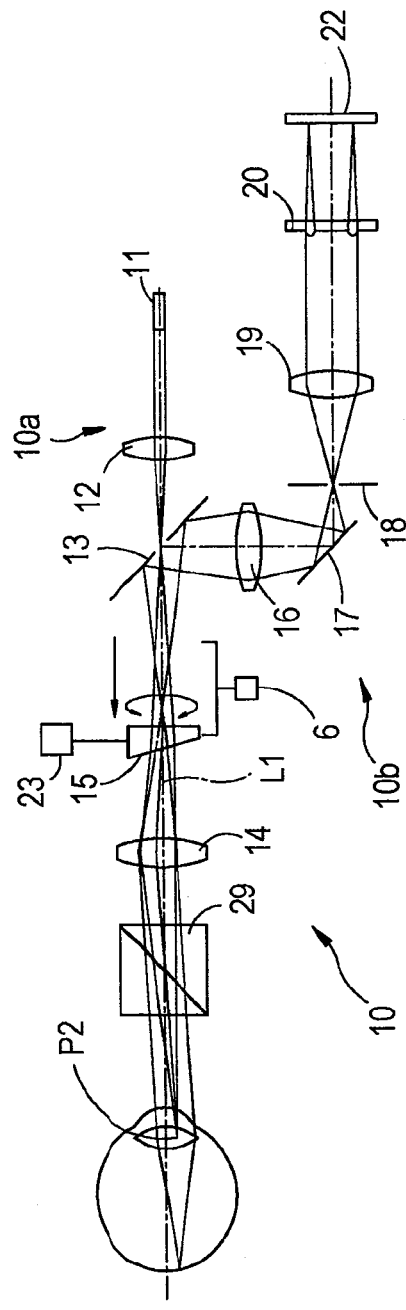
FIG. 2A
FIG. 2B

EYE REFRACTIVE POWER MEASUREMENT APPARATUS

CROSS-REFERENCE TO RELATED APPLICATION

This application is based on Japanese Patent Application No. 2009-227808 filed with the Japan Patent Office on Sep. 30, 2009, the entire content of which is hereby incorporated by reference.

BACKGROUND

1. Technical Field

The present invention relates to an eye refractive power measurement apparatus for objectively measuring a refractive power of an examinee's eye.

2. Related Art

There has been known an eye refractive power measurement apparatus that includes a measuring optical system for projecting measurement light onto a fundus of an examinee's eye, extracting as ring-shaped light the measurement light reflected from the fundus, and causing a two-dimensional imaging device to capture a ring-shaped image (refer to JP 2005-185523 A). In this apparatus, a light deflecting member is arranged rotatably on a common optical path of a light projecting optical system for projecting the measurement light and a light receiving optical system for receiving the measurement light. Thus, this apparatus allows measurement of an average refractive power in a pupil of the examinee's eye.

In daily life, a diameter of a pupil of an eye varies when ambient brightness differs at day and night or in an indoor environment and an outdoor environment. For this reason, there is required an objective inspection (measurement) for refractive powers according to different diameters of the pupil.

However, the conventional apparatus merely measures an eye refractive power, based on a fixed diameter (e.g., 4 mm) of the pupil for the following reason. That is, the conventional apparatus is incapable of changing a measurement range for the eye refractive power.

SUMMARY

A technical object of the present invention is to provide an eye refractive power measurement apparatus capable of easily measuring a refractive power of an examinee's eye in a case where a pupil is small in diameter and a refractive power of the same examinee's eye in a case where the pupil is large in diameter.

In order to accomplish this object, the present invention provides the following configurations.

That is, an eye refractive power measurement apparatus includes: a measuring optical system that projects measurement light onto a fundus of an examinee's eye, extracts as ring-shaped light the measurement light reflected from the fundus, and causes an imaging device to capture a ring-shaped image; a light deflecting member that is arranged at a position, which is out of a conjugated position with a pupil of the examinee's eye, on an optical path of the measuring optical system; a rotor that causes the light deflecting member to rotate about an optical axis of the measuring optical system; and an eccentricity amount changer that changes an amount of eccentricity of the measurement light, which is rotated eccentrically on a surface of the pupil, with respect to a center of the pupil, in order to change a region, where the measurement light passes, on the surface of the pupil through which the measurement light passes.

Preferably, the eye refractive power measurement apparatus further includes a calculator that measures refractive powers of the examinee's eye, based on ring-shaped images to be obtained prior to and subsequent to the change of the amount of eccentricity by the eccentricity amount changer.

Preferably, the eye refractive power measurement apparatus further includes a mode switch that switches between a first measurement mode for measuring a refractive power of an examinee's eye in a case where a pupil is small in diameter and a second measurement mode for measuring a refractive power of the same examinee's eye in a case where the pupil is large in diameter. Herein, the eccentricity amount changer changes the amount of eccentricity between a first amount of eccentricity which corresponds to the first measurement mode and a second amount of eccentricity which corresponds to the second measurement mode and is larger than the first amount of eccentricity, based on a switching signal from the mode switch.

Preferably, the eccentricity amount changer includes a shifter that causes the light deflecting member to move in a direction of the optical axis, and the shifter causes the light deflecting member to move away from the conjugated position with the pupil when the mode switch outputs a switching signal for switching the first measurement mode to the second measurement mode.

Preferably, the eccentricity amount changer includes a shifter that causes the light deflecting member to move in a direction of the optical axis.

BRIEF DESCRIPTION OF THE DRAWINGS

The foregoing and other objects, features, aspects and advantages of the invention will become more apparent from the following detailed description when taken in conjunction with the accompanying drawings, in which:

FIG. 2A illustrates a schematic configuration of the optical system prior to a movement of a prism, and FIG. 2B illustrates a schematic configuration of the optical system subsequent to the movement of the prism;

DESCRIPTION OF EMBODIMENTS

Figure 1:
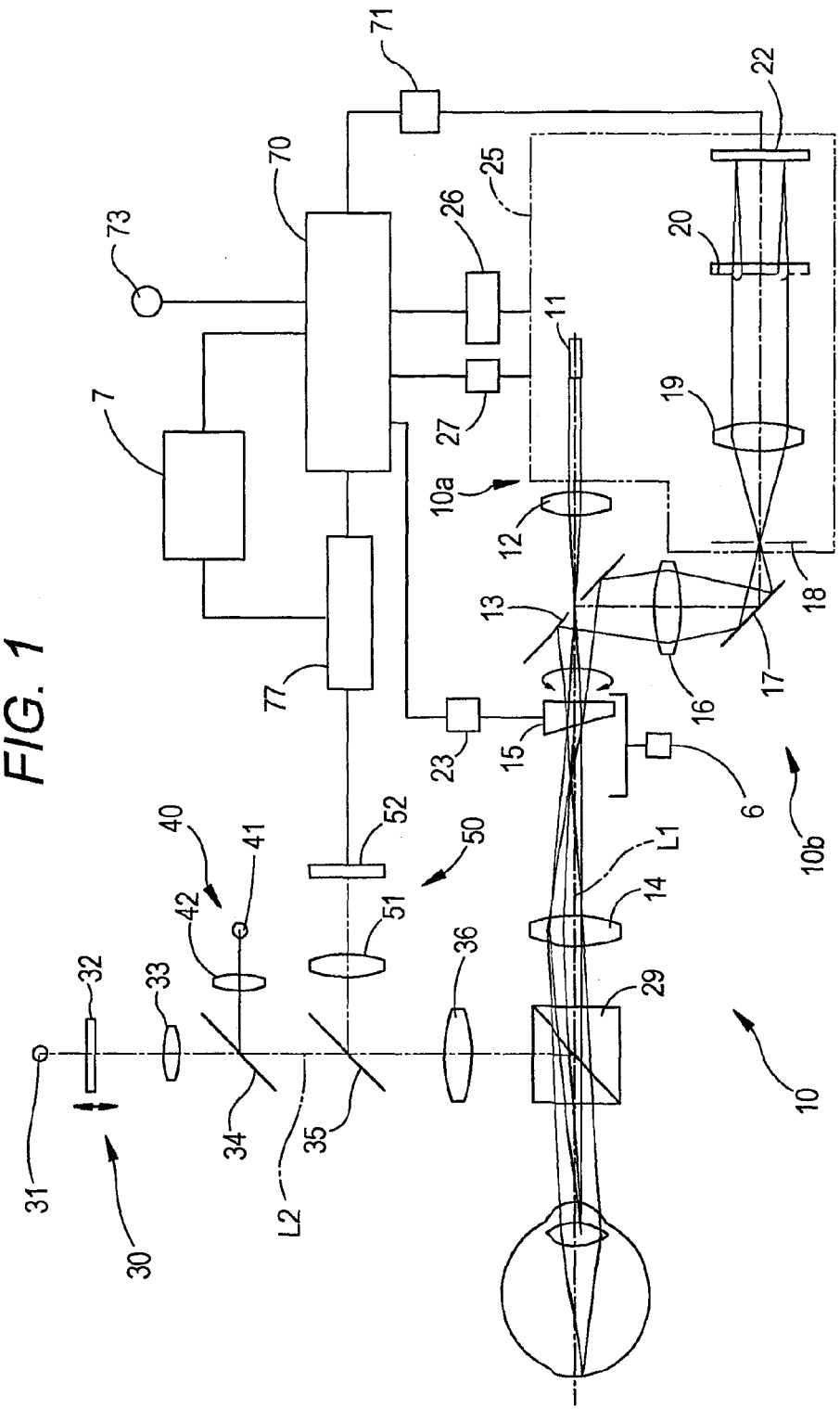
FIG. 1 illustrates a schematic configuration of an optical system and a control system in an eye refractive power measurement apparatus according to one embodiment of the present invention.

Preferred embodiments of the present invention will be described below with reference to the accompanying drawings, in which like reference characters designate similar or identical parts throughout the several views thereof. FIG. 1 illustrates a schematic configuration of an optical system and a control system in an eye refractive power measurement apparatus according to one embodiment of the present invention. A measuring optical system 10 includes a light projecting optical system 10a and a light receiving optical system 10b. The light projecting optical system 10a projects spot-shaped measurement light onto a fundus of an examinee's eye via a center of a pupil of the examinee's eye. The light receiving optical system 10b extracts the measurement light reflected from the fundus, as ring-shaped light, from a peripheral portion of the pupil, and causes a two-dimensional imaging device to capture a ring-shaped image.

The light projecting optical system 10a includes an infrared point light source 11 such as an LED (Light Emitting Diode) or an SLD (Super Luminescent Diode), a relay lens 12, a hole mirror 13, a prism 15 serving as a light deflecting member, and an objective lens 14 for measurement. Herein, these members 11 to 15 are arranged on a measurement optical axis L1. The light source 11 is arranged at a conjugated position with the fundus. Moreover, the hole mirror 13 has a hole located at a conjugated position with the pupil. The prism 15 is arranged at a position out of the conjugated position with the pupil, and deflects light, which passes therethrough, with respect to the optical axis L1. Further, the prism 15 is rotated about the optical axis L1 by a driving part 23 configured with a motor and the like. In place of the prism 15, a parallel planar plate may be arranged obliquely on the optical axis L1. A beam splitter 29 is arranged between the objective lens 14 and the examinee's eye to serve as an optical path dividing member. The beam splitter 29 guides light reflected from an anterior segment of the examinee's eye to an observing optical system 50, and also guides light from a fixation index optical system 30 to the fundus.

The objective lens 14, the prism 15 and the hole mirror 13 are shared between the light projecting optical system 10a and the light receiving optical system 10b. The light receiving optical system 10b also includes a relay lens 16 and a total reflection mirror 17 which are arranged on an optical path in a direction of reflection by the hole mirror 13. The light receiving optical system 10b also includes a light receiving aperture 18, a collimator lens 19, a ring lens 20, and a two-dimensional imaging device (a light receiving device) 22 such as a CCD (Charge Coupled Device). These members 18, 19, 20 and 22 are arranged on an optical path along a direction of reflection by the mirror 17. Each of the aperture 18 and the imaging device 22 is arranged at a conjugated position with the fundus. An output signal from the imaging device 22 is input to a calculation control part 70 through an image processing part 71.

The ring lens 20 includes a lens portion (a light transmitting portion) configured with a ring-shaped cylindrical lens formed on a flat plate, and a light shielding portion corresponding to a portion other than the lens portion. This light shielding portion is subjected to coating in order to shield light, and defines a ring-shaped opening. The ring lens 20 is arranged such that the light shielding portion is located at a conjugated position with the pupil. However, this position is not necessarily conjugated with the pupil in a strict sense as long as the light shielding portion is conjugated with the pupil with a required accuracy in view of a measurement accuracy. For this reason, the reflected light from the fundus is extracted as ring-shaped light having a size corresponding to the light shielding portion, from the peripheral portion of the pupil. When the ring lens 20 receives parallel light, a ring-shaped image which is equal in size to the ring lens 20 is formed on the imaging device 22 arranged on a focus position of the parallel light. Herein, the light shielding portion having the ring-shaped opening may be configured as a different member in the vicinity of the ring lens 20.

The light source 11 of the light projecting optical system 10a as well as the aperture 18, the collimator lens 19, the ring lens 20 and the imaging device 22 of the light receiving optical system 10b are movable integrally as a movable unit 25 in the direction of the optical axis L1. A driving part 26 configured with a motor and the like causes the movable unit 25 to move in accordance with a spherical refractive error (a spherical refractive power) of the examinee's eye. Specifically, the driving part 26 arranges each of the light source 11, the aperture 18 and the imaging device 22 at an optically conjugated position with the fundus to correct the spherical refractive error. A potentiometer 27 detects a position of the movable unit 25 thus moved. Herein, each of the hole mirror 13 and the ring lens 20 is arranged at an optically conjugated position with the pupil at a fixed magnification irrespective of the amount of movement of the movable unit 25.

Infrared measurement light emitted from the light source 11 transmits through the relay lens 12, passes through the hole of the hole mirror 13, and transmits through the prism 15, the objective lens 14 and the beam splitter 29, so that a spot-shaped point light source image is formed on the fundus. Herein, since the prism 15 rotates about the optical axis L1, a pupil projection image in the hole of the hole mirror 13 (projected light on the surface of the pupil) is rotated eccentrically at high speed. The point light source image projected on the fundus is reflected and scattered at the fundus, is emerged from the examinee's eye, and then is collected by the objective lens 14. Thereafter, this light transmits through the prism 15, is reflected by a peripheral surface of the hole of the hole mirror 13, transmits through the relay lens 16, is reflected by the total reflection mirror 17, and is collected by the aperture 18 again. Based on this light, a ring-shaped image is formed on the imaging device 22 through the collimator lens 19 and the ring lens 20. An output signal from the imaging device 22 is detected and processed by the image processing part 71.

The prism 15 is arranged on the common optical path of the light projecting optical system 10a and the light receiving optical system 10b. Therefore, the reflected light from the fundus passes through the prism 15 of the light projecting optical system 10a. In the optical system subsequent to the prism 15, accordingly, the reflected light is in such a state that each of the projected light on and the reflected light (the received light) from the surface of the pupil undergoes no eccentricity.

Moreover, a driving part 6 configured with a motor and the like causes the prism 15 to move in the direction of the optical axis L1. In other words, the driving part 6 is used for changing the position of the prism 15 in accordance with a measurement mode (to be described later). FIG. 2A illustrates an optical layout before the driving part 6 changes the position of the prism 15, and FIG. 2B illustrates an optical layout after the driving part 6 changes the position of the prism 15. As illustrated in FIGS. 2A and 2B, the driving part 6 causes the prism 15 to move away from the conjugated position with the pupil. Thus, the driving part 6 changes the position where the prism 15 deflects the light. Hence, it is possible to produce an advantage of changing an amount of eccentricity of ring-shaped light to be formed on the surface of the pupil (i.e., changing a center of the ring-shaped light from a position P1 to a position P2). In other words, the ring-shaped light on the surface of the pupil is located at a position which is distant from the center of the pupil as compared with the position illustrated in FIG. 2A (see FIG. 2B).

The beam splitter 29 causes an optical axis L2 to be coaxial with the optical axis L1. An objective lens 36 for observation, a half mirror 35, a dichroic mirror 34 having a characteristic of allowing visible light to transmit therethrough, but reflecting infrared light, a light projecting lens 33, a fixation index 32 and a visible light source 31 are arranged on the optical axis L2. These members 31 to 36 form the fixation index optical system 30. Each of the light source 31 and the fixation index 32 moves in a direction of the optical axis L2 to cause the examinee's eye to fog. The light source 31 illuminates the fixation index 32 with visible light. The light from the fixation index 32 transmits through the light projecting lens 33, the dichroic mirror 34, the half mirror 35 and the objective lens 36, is reflected by the beam splitter 29, and is projected onto the fundus. Thus, the examinee's eye fixates the fixation index 32.

In an optical system 40 for projecting an alignment index from a front side of the examinee's eye, infrared light from an infrared point light source 41 is collected by a condenser lens 42. Then, this infrared light is reflected by the dichroic mirror 34, and transmits through the half mirror 35 and the objective lens 36 to turn into substantially parallel light. Thereafter, the parallel light is reflected by the beam splitter 29, and is projected onto the anterior segment.

In the observing optical system 50, an imaging lens 51 and a two-dimensional imaging device (a light receiving device) 52 such as a CCD are arranged on an opposite side to the half mirror 35. An output signal from the imaging device 52 is input to an image processing part 77, and an image output from the image processing part 77 is displayed on a monitor 7. Light from a light source (not illustrated) for illuminating the anterior segment is reflected by the anterior segment, is reflected by the beam splitter 29, transmits through the objective lens 36, is reflected by the half mirror 35, and enters the imaging lens 51. Then, an anterior segment image is formed on the imaging device 52 through the imaging lens 51. The anterior segment image captured by the imaging device 52 is displayed on the monitor 7. The observing optical system 50 serves as both an optical system for detecting an alignment index image formed on a cornea and an optical system for detecting a position of a pupil. In the observing optical system 50, the image processing part 77 detects the position of the alignment index image and the position of the pupil.

The calculation control part 70 analyses a ring-shaped image acquired by the image processing part 71, and calculates a refractive power of the examinee's eye. Moreover, the calculation control part 70 controls the entire apparatus. A mode selection switch 73 is connected to the calculation control part 70. Upon measurement of refractive powers of a single examinee's eye, the mode selection switch 73 switches between a first measurement mode for measuring an eye refractive power in a case where it is assumed that a pupil is small in diameter (e.g., 4 mm) and a second measurement mode for measuring an eye refractive power in a case where it is assumed that the pupil is large in diameter (e.g., 6 mm).

The following description is given about operations of the apparatus configured as described above. When the mode selection switch 73 selects the first measurement mode, the calculation control part 70 controls the driving part 6 such that the driving part 6 causes the prism 15 to move to a first position corresponding to the first measurement mode (e.g., a position where a measurement range on the surface of the pupil is not more than 4 mm in diameter in this embodiment) (see FIG. 2A).

The measurement optical axis L1 is aligned with the center of the pupil (or the center of the cornea) of the examinee's eye, so that a trigger signal indicating a start of measurement is output to the calculation control part 70. Then, the calculation control part 70 actuates the light source 11 and, further, controls the driving part 23 such that the driving part 23 causes the prism 15 to rotate at high speed.

Figure 3A:
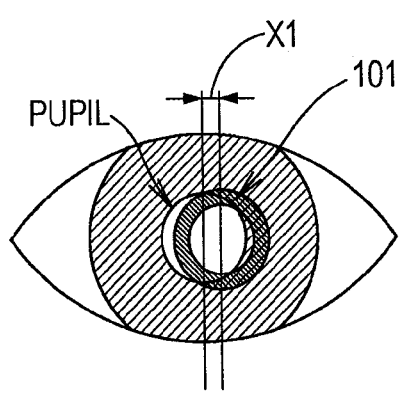
FIG. 3A illustrates ring-shaped light prior to the movement of the prism.

As illustrated in FIG. 3A, in this case, of the reflected light from the fundus, ring-shaped light 101 extracted by the ring lens 20 from the surface of the pupil is formed about a position which is spaced away from the center of the pupil by a distance X1. When the driving part 23 causes the prism 15 to rotate eccentrically at high speed, the ring-shaped light 101 shifts at high speed on a circumference which is spaced away from the center of the pupil by the distance X1.

Figure 4A:
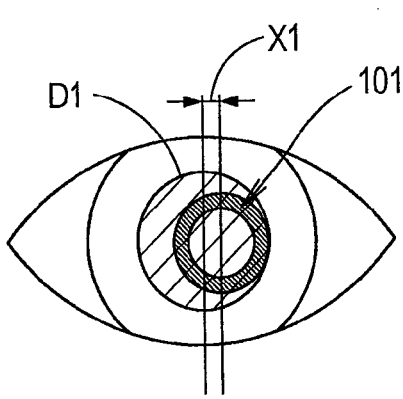
FIG. 4A illustrates a measurement region prior to the movement of the prism.

Then, when the prism 15 rotates at high speed in a cycle which is shorter than an accumulation time of the imaging device 22, the ring-shaped light 101 passes through a measurement region D1 (e.g., not more than 4 mm in diameter) illustrated in FIG. 4A. Finally, the ring-shaped light 101 is detected as a ring-shaped image which is obtained in such a manner that the ring-shaped light 101 entering the imaging device 22 is subjected to integration by the imaging device 22. Then, the calculation control part 70 determines an eye refractive power from the ring-shaped image acquired by the imaging device 22, and displays the eye refractive power on the monitor 7. Thus, it is possible to obtain an average refractive power of the single examinee's eye in the measurement region D1 in the case where it is assumed that the pupil is small in diameter. Hence, it is possible to measure an eye refractive power in the case where the pupil is small in diameter.

The eye refractive power in the case where the pupil is small in diameter is measured as described above. Thereafter, when the mode selection switch 73 generates a switching signal for switching the first measurement mode to the second measurement mode (herein, these modes may be switched automatically), the calculation control part 70 controls the driving part 6 such that the driving part 6 causes the prism 15 to move away from the conjugated position with the pupil. Thus, the prism 15 moves to a second position corresponding to the second measurement mode (e.g., a position where a measurement range on the surface of the pupil is not more than 6 mm in diameter in this embodiment) (see FIG. 2B). As a result, a position where the prism 15 deflects light varies, so that an amount of eccentricity of ring-shaped light on the surface of the pupil increases (i.e., an amount of eccentricity of ring-shaped light is changed from a first amount of eccentricity to a second amount of eccentricity).

Figure 3B:
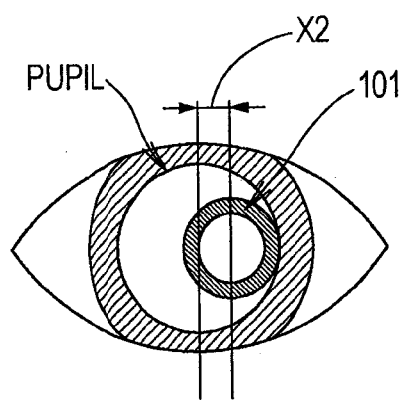
FIG. 3B illustrates the ring-shaped light which is changed in amount of eccentricity subsequent to the movement of the prism.

As illustrated in FIG. 3B, in this case, ring-shaped light 101 is formed about a position which is spaced away from the center of the pupil by a distance X2 (X1<X2). When the driving part 23 causes the prism 15 to rotate eccentrically at high speed, the ring-shaped light 101 shifts at high speed on a circumference which is spaced away from the center of the pupil by the distance X2.

Figure 4B:
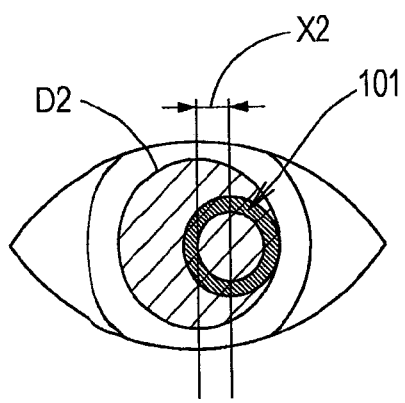
FIG. 4B illustrates the measurement region which is changed in the amount of eccentricity subsequent to the movement of the prism.

Then, when the prism 15 rotates at high speed as in the first measurement mode, the ring-shaped light 101 passes through a measurement region D2 (e.g., not more than 6 mm in diameter) illustrated in FIG. 4B. The calculation control part 70 determines an eye refractive power from the ring-shaped image acquired by the imaging device 22, and displays the eye refractive power on the monitor 7. Thus, it is possible to obtain an average refractive power of the single examinee's eye in the measurement region D2 in the case where it is assumed that the pupil is large in diameter. Hence, it is possible to measure an eye refractive power in the case where the pupil is large in diameter.

As described above, the switch between the first measurement mode and the second measurement mode allows the change of the measurement region (the measurement range) on the surface of the pupil. Therefore, it is possible to measure a refractive power of an examinee's eye in a case where it is assumed that a pupil is small in diameter and a refractive power of the same examinee's eye in a case where it is assumed that the pupil is large in diameter.

The configuration of the eye refractive power measurement apparatus is not limited to that described above as long as the amount of eccentricity of the ring-shaped light on the surface of the pupil can increase in the second measurement mode as compared with the first measurement mode. For example, the eye refractive power measurement apparatus may be configured to increase a tilt angle of the prism 15 relative to the optical axis L1 in the second measurement mode.

Figure 5:
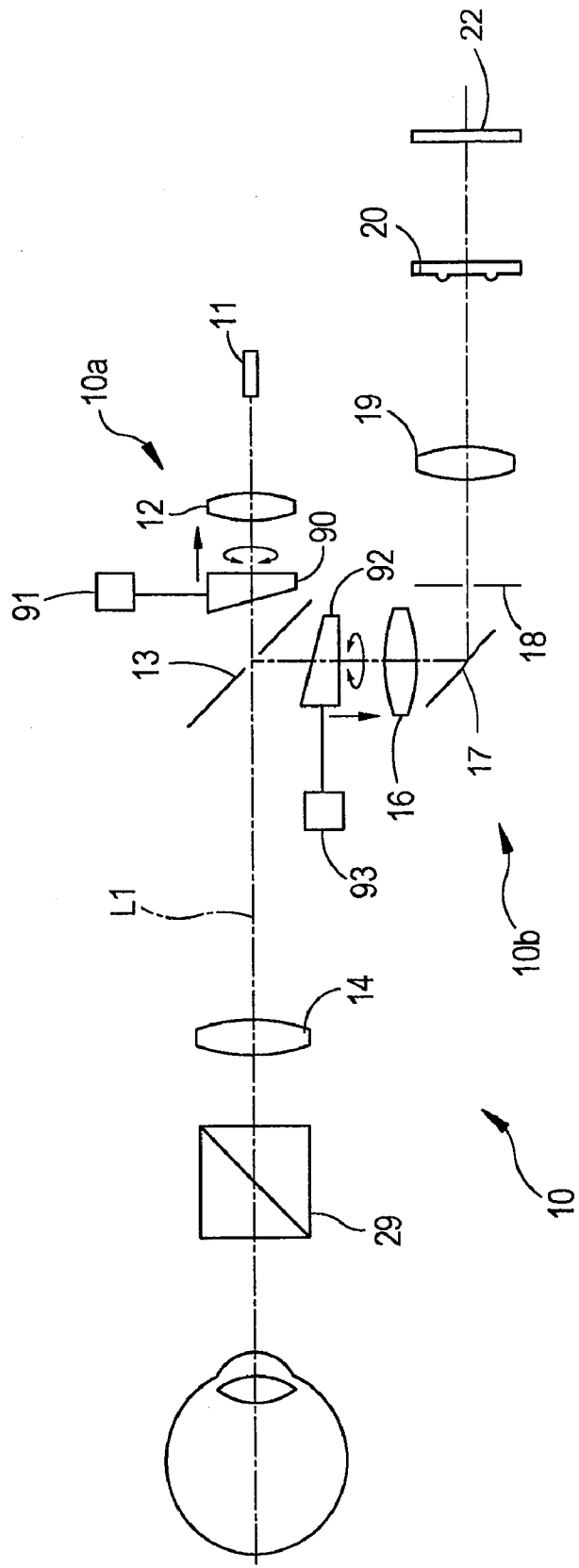
FIG. 5 illustrates a schematic configuration of a measuring optical system according to a modification example.

Alternatively, the eye refractive power measurement apparatus according to the present invention may adopt a configuration illustrated in FIG. 5. As illustrated in FIG. 5, in this configuration, a first prism 90 serving as a light deflecting member is interposed between the relay lens 12 and the hole mirror 13 on a dedicated optical path of the light projecting optical system 10a. Further, a second prism 92 serving as a light deflecting member is interposed between the hole mirror 13 and the relay lens 16 on a dedicated optical path of the light receiving optical system 10b. In this configuration, moreover, a driving part 91 causes the prism 90 to rotate about the optical axis L1 of the light projecting optical system 10a, and a driving part 93 causes the prism 92 to rotate about the optical axis L1 of the light receiving optical system 10b. Herein, the driving parts 91 and 93 cause the prisms 90 and 92 to rotate in synchronization with each other such that the prisms 90 and 92 are equal in direction of deflection to each other. Each of the prisms 90 and 92 is arranged at a position out of the conjugated position with the pupil. In this case, the first measurement mode is switched to the second measurement mode in such a manner that each of the prisms 90 and 92 is moved away from the conjugated position with the pupil.

Moreover, the configuration of the measuring optical system is not limited to that described above. For example, a publicly known measuring optical system may be used. Such a publicly known measuring optical system projects ring-shaped measurement light onto a fundus via a peripheral portion of a pupil, extracts light reflected from the fundus through a center of the pupil, and causes a two-dimensional imaging device to form a ring-shaped image. In addition, the measuring optical system may extract an intermittent ring-shaped image rather than a continuous ring-shaped image. Furthermore, the measuring optical system may extract dot images arranged in a ring shape.

While the invention has been illustrated and described in detail, the foregoing description is in all aspects illustrative and not restrictive. It is therefore understood that numerous modifications and variations can be devised without departing from the spirit and scope of the invention.

What is claimed is:

1. An eye refractive power measurement apparatus comprising:
    a measuring optical system that projects measurement light onto a fundus of an examinee's eye, extracts as ring-shaped light the measurement light reflected from the fundus, and causes an imaging device to capture a ring-shaped image;
    a light deflecting member that is arranged at a position, which is out of a conjugated position with a pupil of the examinee's eye, on an optical path of the measuring optical system;
    a rotor that causes the light deflecting member to rotate about an optical axis of the measuring optical system; and
    an eccentricity amount changer that changes an amount of eccentricity of the measurement light, which is rotated eccentrically on a surface of the pupil, with respect to a center of the pupil, in order to change a region, where the measurement light passes, on the surface of the pupil through which the measurement light passes.

2. The eye refractive power measurement apparatus according to claim 1, further comprising
    a calculator that measures refractive powers of the examinee's eye, based on ring-shaped images to be obtained prior to and subsequent to the change of the amount of eccentricity by the eccentricity amount changer.

3. The eye refractive power measurement apparatus according to claim 2, further comprising
    a mode switch that switches between a first measurement mode for measuring a refractive power of an examinee's eye in a case where a pupil is small in diameter and a second measurement mode for measuring a refractive power of the same examinee's eye in a case where the pupil is large in diameter, wherein
    the eccentricity amount changer changes the amount of eccentricity between a first amount of eccentricity which corresponds to the first measurement mode and a second amount of eccentricity which corresponds to the second measurement mode and is larger than the first amount of eccentricity, based on a switching signal from the mode switch.

4. The eye refractive power measurement apparatus according to claim 3, wherein
    the eccentricity amount changer includes a shifter that causes the light deflecting member to move in a direction of the optical axis, and
    the shifter causes the light deflecting member to move away from the conjugated position with the pupil when the mode switch outputs a switching signal for switching the first measurement mode to the second measurement mode.

5. The eye refractive power measurement apparatus according to claim 1, wherein
    the eccentricity amount changer includes a shifter that causes the light deflecting member to move in a direction of the optical axis.

6. An eye refractive power measurement apparatus comprising:
    a measuring optical system that projects measurement light onto a fundus of an examinee's eye, extracts as ring-shaped light the measurement light reflected from the fundus, and causes an imaging device to capture a ring-shaped image;
    a light deflecting member that is arranged at a position, which is out of a conjugated position with a pupil of the examinee's eye, on an optical path of the measuring optical system; and
    a rotor that causes the light deflecting member to rotate about an optical axis of the measuring optical system, wherein
    the measuring optical system rotates the measurement light in each of a first measurement region on the pupil of the examinee's eye in the case where it is assumed that the pupil is small in diameter and a second measurement region on the pupil of the examinee's eye, which is larger than the first measurement region, in the case where it is assumed that the pupil is large in diameter, by rotation of the light deflecting member to obtain an average refractive power in the first measurement region and an average refractive power in the second measurement region.

* * * * *